United States Patent
Adam et al.

(10) Patent No.: US 12,011,536 B2
(45) Date of Patent: Jun. 18, 2024

(54) DISPENSING ASSEMBLY COMPRISING A LATERAL ACTUATION DEVICE FOR A FLUID PRODUCT DISPENSER

(71) Applicant: APTAR FRANCE SAS, Le Neubourg (FR)

(72) Inventors: Fabien Adam, Aviron (FR); Lila Graine, Beynes (FR)

(73) Assignee: APTAR FRANCE SAS, Le Neubourg (FR)

( * ) Notice: Subject to any disclaimer, the term of this patent is extended or adjusted under 35 U.S.C. 154(b) by 250 days.

(21) Appl. No.: 17/630,366

(22) PCT Filed: Jul. 20, 2020

(86) PCT No.: PCT/FR2020/051301
§ 371 (c)(1),
(2) Date: Jan. 26, 2022

(87) PCT Pub. No.: WO2021/019145
PCT Pub. Date: Feb. 4, 2021

(65) Prior Publication Data
US 2022/0362488 A1    Nov. 17, 2022

(30) Foreign Application Priority Data
Jul. 26, 2019 (FR) ...................................... 1908524

(51) Int. Cl.
*A61M 11/00* (2006.01)
*A61M 15/00* (2006.01)
(Continued)

(52) U.S. Cl.
CPC ...... *A61M 11/007* (2014.02); *A61M 15/0025* (2014.02); *A61M 15/009* (2013.01);
(Continued)

(58) Field of Classification Search
CPC ............ A61M 11/007; A61M 15/0025; A61M 15/009; A61M 31/00; A61M 2205/276
See application file for complete search history.

(56) References Cited

U.S. PATENT DOCUMENTS

| 3,084,871 A | 4/1963 | Puglis |
| 3,478,935 A | 11/1969 | Brooks |

(Continued)

FOREIGN PATENT DOCUMENTS

| EP | 1 974 829 A1 | 10/2008 |
| GB | 1 531 308 A | 11/1978 |

(Continued)

OTHER PUBLICATIONS

International Search Report for PCT/FR2020/051301 dated Nov. 4, 2020 [PCT/ISA/210].

(Continued)

*Primary Examiner* — Jeremy Carroll
(74) *Attorney, Agent, or Firm* — Sughrue Mion, PLLC

(57) ABSTRACT

Dispensing assembly, comprising a fluid product dispenser, such as a nasal dispenser, wherein the fluid product dispenser comprises a reservoir (10) provided with a bottom (11), a dispensing member (20), such as a pump or a valve, mounted on the reservoir (10), and a dispensing head (30) incorporating a dispensing orifice (31), the dispensing assembly comprising a lateral actuation device comprising a body (1) and a lateral actuation element (40) mounted so as to pivot on the body (1) about a pivot axis (45) between a rest position and an actuation position, the actuation element (40) comprising a bearing part (41), which is pressed by the user during actuation and a pushing part (42) designed to cooperate with the fluid product dispenser to effect the actuation thereof, the pivot axis (45) being arranged between the bearing part (41) and the pushing part (42), the lateral actuation member (40) having an S or inverted S shape, the (Continued)

bearing part (41) being arranged near the dispensing head (30) and the pushing part (42) being arranged under the bottom (11) of the reservoir (10).

8 Claims, 3 Drawing Sheets

(51) Int. Cl.
    *A61M 15/08*     (2006.01)
    *A61M 31/00*     (2006.01)
(52) U.S. Cl.
    CPC ............ *A61M 15/08* (2013.01); *A61M 31/00* (2013.01); *A61M 2205/276* (2013.01); *A61M 2210/0618* (2013.01)

(56) References Cited

U.S. PATENT DOCUMENTS

| | | | | |
|---|---|---|---|---|
| 6,328,035 | B1* | 12/2001 | Wakefield | A61M 15/0093 |
| | | | | 128/200.14 |
| 2004/0245291 | A1* | 12/2004 | Simon | B65D 83/386 |
| | | | | 222/321.7 |
| 2005/0234402 | A1* | 10/2005 | Collins | B05B 11/0038 |
| | | | | 604/151 |
| 2007/0131717 | A1* | 6/2007 | Davies | A61M 15/0001 |
| | | | | 128/200.23 |
| 2008/0177246 | A1* | 7/2008 | Sullivan | A61M 5/30 |
| | | | | 604/116 |
| 2022/0409830 | A1* | 12/2022 | Shahaf | B05B 11/062 |

FOREIGN PATENT DOCUMENTS

| | | |
|---|---|---|
| WO | 03/103760 A1 | 12/2003 |
| WO | 2014/077839 A1 | 5/2014 |

OTHER PUBLICATIONS

Written Opinion for PCT/FR2020/051301 dated Nov. 4, 2020 [PCT/ISA/237].

International Preliminary Report on Patentability dated Jun. 9, 2021 in Application No. PCT/FR2020/051301.

\* cited by examiner

DISPENSING ASSEMBLY COMPRISING A LATERAL ACTUATION DEVICE FOR A FLUID PRODUCT DISPENSER

CROSS REFERENCE TO RELATED APPLICATIONS

This application is a National Stage of International Application No. PCT/FR2020/051301 filed Jul. 20, 2020, claiming priority based on French Patent Application No. 1908524 filed Jul. 26, 2019.

FIELD OF THE INVENTION

The present invention relates to a dispensing assembly comprising a lateral actuation device for actuating a fluid product dispenser, in particular a nasal spray device of a pharmaceutical product.

DESCRIPTION OF RELATED ART

Fluid product dispensers are well-known in the state of the art. They generally comprise a reservoir containing the fluid product on which a dispensing member is assembled, for example a pump or a valve, which is generally actuated by means of a dispensing head for selectively dispensing the product contained inside said reservoir. The dispensing head comprises a dispensing orifice through which the product will be sprayed, for example in the nose of the user in the case of a nasal spray device. Numerous devices of this type are actuated manually by the user by axially moving against one another, the reservoir and the dispensing head, which has the effect of actuating the dispensing member. This type of device however has disadvantages, in particular when the device is of the nasal spray type, as the axial force exerted by the user to actuate the device induces a risk of moving the dispensing head inside the nostril of the user, with risks of injury and/or incomplete or inadequate dispensing of the product at the time of the actuation.

To overcome this problem, lateral actuation devices have been proposed, generally comprising a lever mounted so as to pivot on a body and an inner part of which is designed to cooperate with one from among the dispensing head or the reservoir to move this element against the other and thus actuate the dispensing member. A disadvantage of this type of lateral actuation devices is the excess cost that it represents for the fluid product dispenser. Another disadvantage is the bulk, in particular in the lateral direction, of the lateral actuation device.

Documents EP1974829, U.S. Pat. No. 3,478,935, WO2014077839, WO03103760 and GB1531308 describe devices of the state of the art.

Certain Objects and Advantages of the Invention

The present invention aims to provide a dispensing assembly comprising a lateral actuation device which does not reproduce the abovementioned disadvantages.

The present invention also aims to provide such a lateral actuation device which can be used with several fluid product dispensers, thus limiting its excess cost, while guaranteeing a certain and reliable actuation of the fluid product dispenser on each actuation, without risk of injury for the user.

More specifically, the present invention aims to provide a dispensing assembly comprising a lateral actuation device which is simple and inexpensive to manufacture and to assemble.

The present invention therefore aims for a dispensing assembly, comprising a fluid product dispenser, such as a nasal dispenser, in which said fluid product dispenser comprises a reservoir provided with a bottom, a dispensing member, such as a pump or a valve, mounted on said reservoir and a dispensing head incorporating a dispensing orifice, said dispensing assembly comprising a lateral actuation device comprising a body and a lateral actuation element mounted so as to pivot on said body about a pivot axis between a rest position and an actuation position, said actuation element comprising a bearing part, which is pressed by the user during actuation, and a pushing part designed to cooperate with said fluid product dispenser to effect the actuation thereof, said pivot axis being arranged between said bearing part and said pushing part, said lateral actuation element having an S or inverted S shape, said bearing part being arranged near said dispensing head and said pushing part being arranged under said bottom of said reservoir.

Advantageously, said actuation element comprises two parallel identical branches connected to one another by said bearing and pushing parts.

Advantageously, said branches comprise a first curvature at their joining to said bearing part and a second curvature, opposite said first curvature, at their joining to said pushing part.

Advantageously, said first and second curvatures are facing towards the inside of said body.

Advantageously, said pivot axis is arranged closer to said pushing part than said bearing part.

Advantageously, a removable protective cap is mounted on said body.

Advantageously, said protective cap comprises an axial extension cooperating with said actuation element to prevent its pivoting.

Advantageously, said pivot axis extends radially outside of said reservoir.

BRIEF DESCRIPTION OF THE DRAWINGS

In a variant, said pivot axis is arranged substantially secant to the longitudinal central axis of said reservoir.

These characteristics and advantages and others of the present invention will appear more clearly in the following detailed description of several embodiments and variants, made in reference to the appended drawings, given as non-limiting examples, in which.

Figure 1:
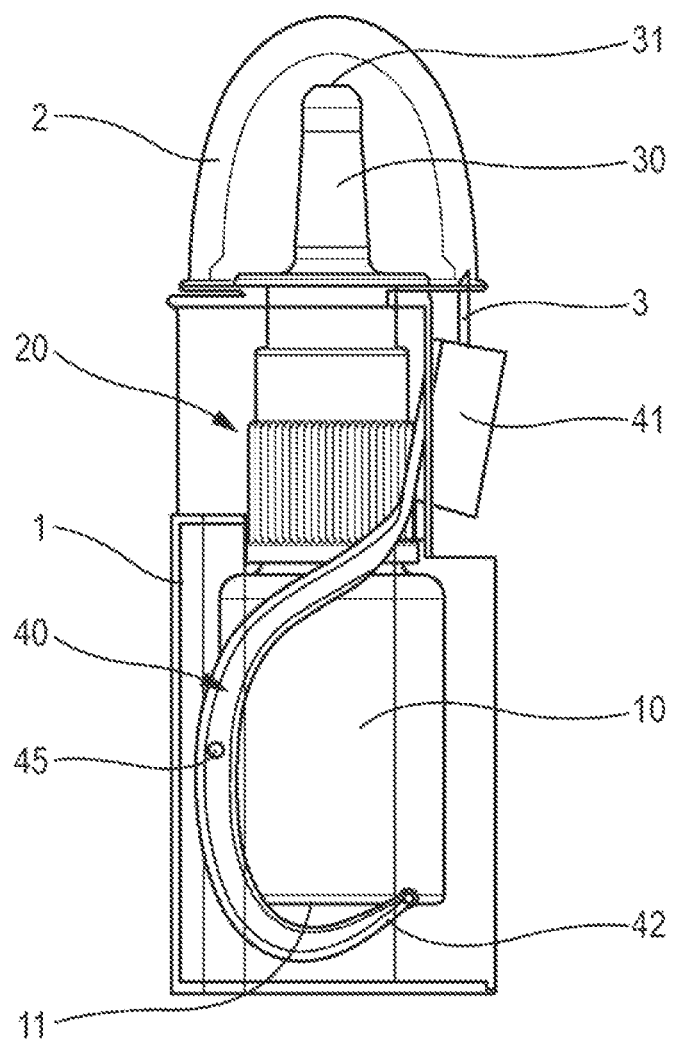
FIG. 1 represents a schematic side view of an assembly according to a first advantageous embodiment, before removal of the protective cap.

Detailed Description of Non-Limiting Embodiment of the Invention

In the description below, the terms "upper", "lower", "top" and "bottom" refer to the right position of the device represented in the Figures. The terms "axial", "lateral" and "radial" refer to the longitudinal central axis of the dispenser.

By referring to the Figures, which illustrate two advantageous embodiments, a dispensing assembly is represented comprising, on the one hand, a lateral actuation device and, on the other hand, a fluid product dispenser, in particular a nasal spray device.

The fluid product dispenser comprises a reservoir 10 which contains the fluid product, in particular the pharmaceutical product designed to be sprayed in the nose of a user. A dispensing member 20, such as a pump or a valve, is assembled on said reservoir 10, by means of a fixing ring (not represented) which is able to be crimped, snap-fitted or screwed. The dispensing member 20, which is not represented in detail in the Figures, conventionally comprises a dispensing member body, such as a pump body or a valve body, and a mobile member, such as a piston rod or a valve, which is axially slidingly mounted in said dispensing member body. Conventionally, the mobile member is pressed inside the dispensing member body, to actuate said dispensing member. A dispensing head 30 is assembled on said dispensing member 20, said dispensing head 30 incorporating a dispensing orifice 31 through which the fluid product is distributed.

A lateral actuation device is provided to be useable with several fluid product dispensers. Thus, the fluid product dispenser is removably mounted in said lateral actuation device, and when the reservoir 10 is empty, the dispenser is removed and replaced by another dispenser comprising a full reservoir 10.

The lateral actuation device comprises a body 1 designed to receive said dispenser. The body 1 can be made of one single piece, or it can comprise two or more parts fixed to one another during the assembly of the dispenser in the body. Below in the description, reference will be made to the body 1, being understood that this comprises the two variants above.

Advantageously, the body 1 is axially open upwards to allow the insertion and the removal of the dispenser through this axial opening. With a body 1 made of several assembled parts, a different assembly direction could be considered.

A removable protective cap 2 is assembled on the body 1 to protect the dispensing orifice 31 between two actuations. This cap 2 can comprise an extension 3 which blocks the actuation of the lateral actuation device when the cap 2 is in place on the body 1. This allows to prevent any accidental actuation, for example during transport.

The lateral actuation device comprises a lateral actuation element 40 rigidly connected to the body 1 and designed to cooperate with the reservoir 10. This lateral actuation element 40 comprises a bearing part 41 which the user presses to actuate the dispenser, and a pushing part 42 cooperating with the bottom 11 of the reservoir 10. The lateral actuation element 40 is mounted so as to pivot on the body 1 about an axis 45.

Figure 2:
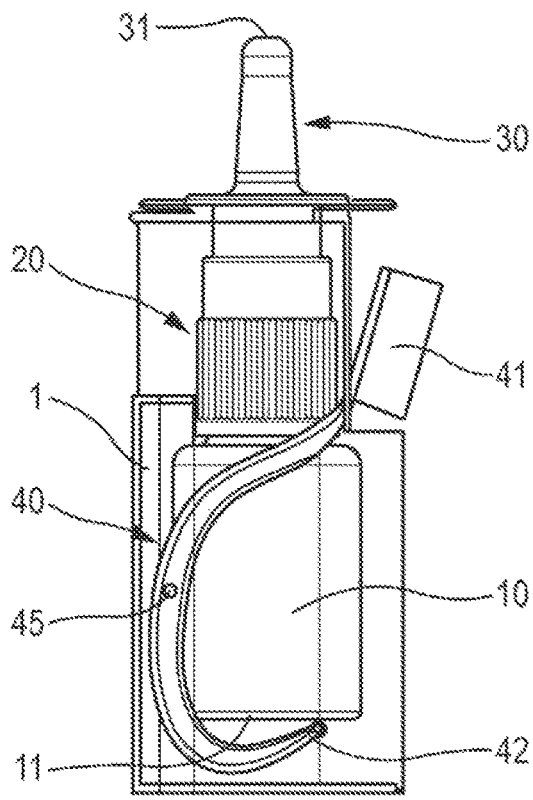
FIGS. 2 and 3 represent schematic side views of the assembly of FIG. 1, respectively in rest position and in actuated position.
Figure 3:
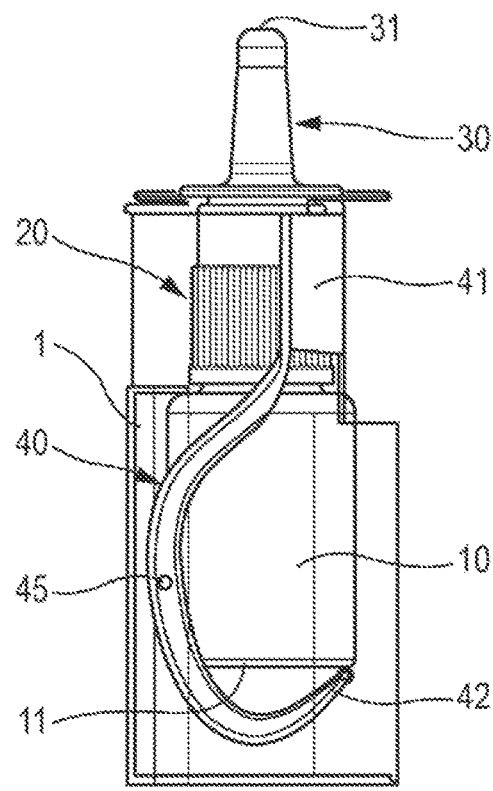

According to the invention, the lateral actuation element 40 has roughly an S or inverted S shape, this second variant being that represented in the drawings. Thus, the bearing part 41 is arranged near the dispensing head 30 and the pushing part 42 is arranged under the bottom 11 of the reservoir 10. The pivot axis 45 is arranged between said bearing part 41 and said pushing part 42. This S or inverted S shape of the actuation element 40 allows to limit its lateral bulk, such that in rest position, which can be seen in FIGS. 2 and 7, the bearing part 41 only extends slightly radially or laterally outside of the body 10. Preferably, the pivot axis 45 is arranged closer to the pushing part 42 than the bearing part 41. This, in particular, allows to optimise the lever effect and therefore to make the actuation easier for the user.

Figure 6:
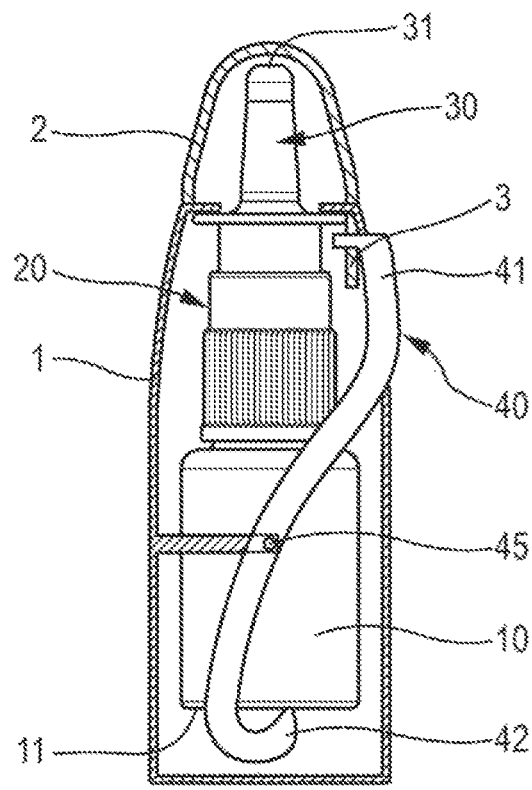
FIG. 6 represents a schematic side view of an assembly according to a second advantageous embodiment, before removal of the protective cap.

As can be seen in FIGS. 1 and 6, when the cap 2 is fixed to the body 1, the axial extension 3 of the cap 2 cooperates with the bearing part 41 of the actuation element 40 to prevent the pivoting of said actuation element.

Figure 4:
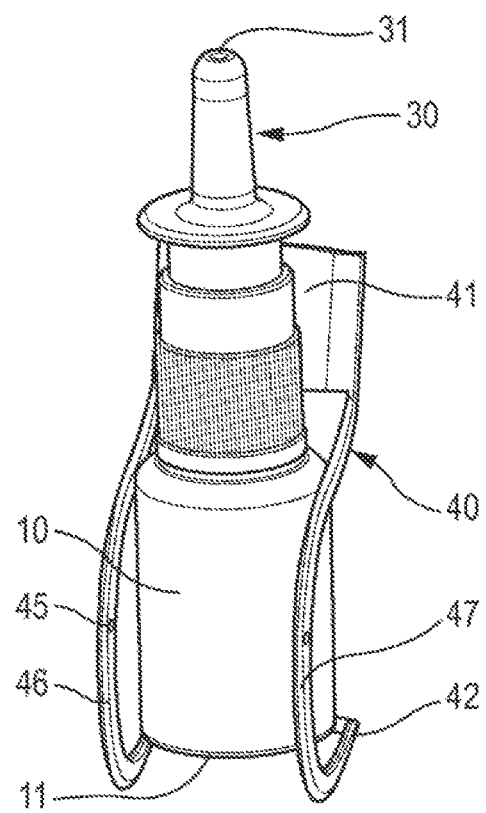
FIGS. 4 and 5 represent schematic, partial perspective views according to two different viewing angles of a lateral actuation element according to an advantageous variant associated with a fluid product dispenser.
Figure 5:
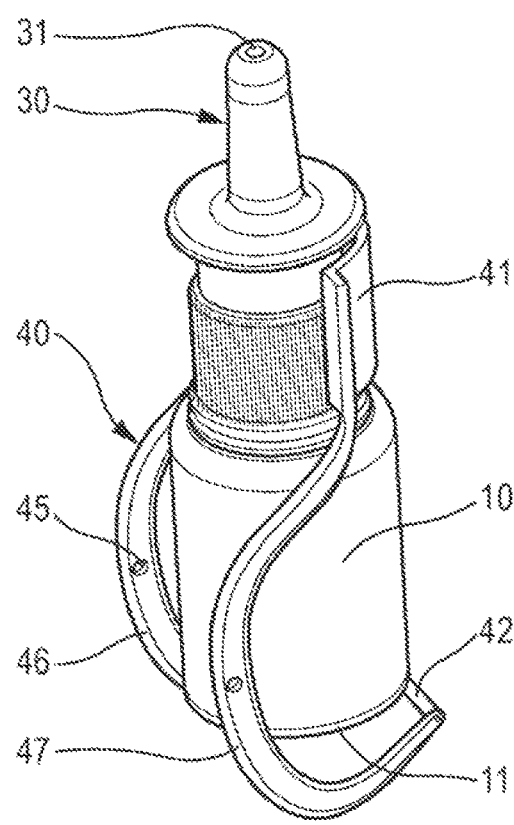

Preferably, the actuation element 40 comprises two parallel identical branches 46, 47 connected to one another by the bearing 41 and pushing 42 parts, which can be seen, in particular, in FIGS. 4 and 5. The first branch 46 extends from one side of the reservoir 10 and the second branch 47 extends from the other side of the reservoir 10. These branches 46, 47 comprise a first curvature at their joining to the bearing part 41 and a second curvature, opposite the first curvature, at their joining to the pushing part 42. As can be seen in the Figures, these two opposite curvatures are both facing towards the inside of the body 1.

Figure 7:
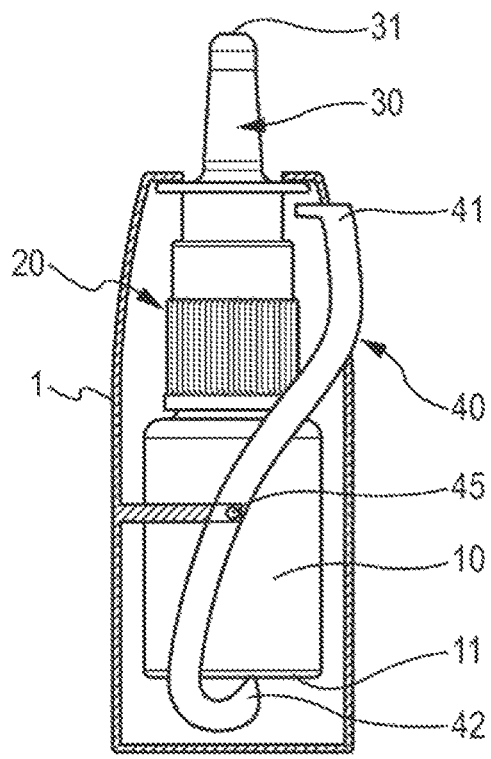
FIGS. 7 and 8 represent schematic side views of the assembly of FIG. 6, respectively in rest position and in actuated position.
Figure 8:
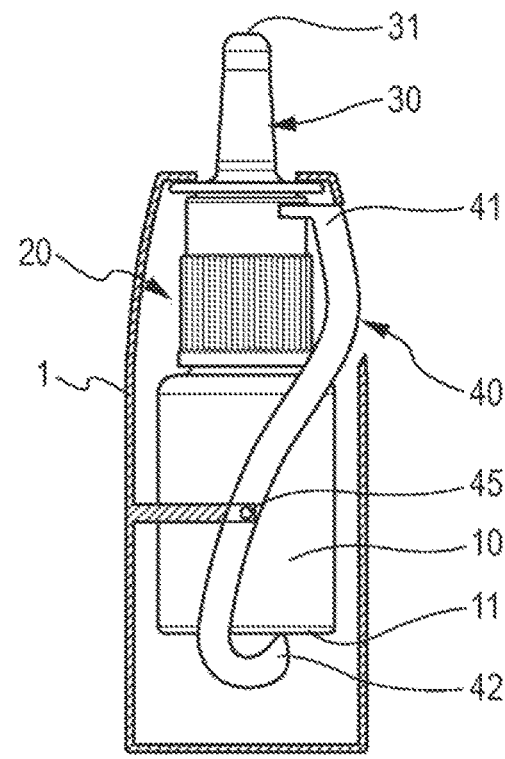

In the embodiment of FIGS. 1 to 5, the pivot axis 45 extends radially outside of the reservoir 10 when a dispenser is assembled in the lateral actuation device. In the embodiment of FIGS. 6 to 8, the pivot axis 45 is arranged substantially secant to the longitudinal central axis of the reservoir 10.

In operation, the user presses on the bearing part 41 of the actuation element 40 to make it pivot with respect to the body 1 about the axis 45. This pivoting of the actuation element 40 causes the axial movement upwards of the pushing part 42 and therefore of the reservoir 10 and thus the actuation of the dispensing member 20.

The actuation element 40 can comprise an elastic element (not represented), such as an elastic strip or a spring, which elastically biases said actuation element 40 towards its rest position. In a variant, the actuation element 40 can be returned to its rest position by the reservoir 10 when it returns to its rest position after each actuation under the effect of the return spring of the dispensing member 20.

Although the invention has been described in reference to embodiments grouping together several of the aspects described above, it is understood that various modifications can be considered for a person skilled in the art without moving away from the scope of the present invention such as defined by the appended claims.

The invention claimed is:

1. A dispensing assembly, comprising a fluid product dispenser, wherein said fluid product dispenser comprises a reservoir provided with a bottom, a dispensing member, such as a pump or a valve, mounted on said reservoir and a dispensing head incorporating a dispensing orifice, said dispensing assembly comprising a lateral actuation device comprising a body and a lateral actuation element mounted on said body to pivot about a pivot axis between a rest position and an actuation position, said actuation element comprising a bearing part, on which the user presses during actuation, and a pushing part adapted to cooperate with said fluid product dispenser to effect actuation thereof, said pivot axis being arranged between said bearing part and said pushing part, said lateral actuation element having a shape of S or inverted S, said bearing part being arranged close to said dispensing head and said pushing part being arranged under said bottom of said reservoir, said actuation element comprising two parallel identical branches connected to one another by said bearing and pushing parts, characterized in that said branches comprise a first curvature at their joining to said bearing part and a second curvature, opposite said first curvature, at their joining to said pushing part.

2. The dispensing assembly according to claim 1, wherein said first and second curvatures are facing towards the inside of said body.

3. The dispensing assembly according to claim 1, wherein said pivot axis is arranged closer to said pushing part than said bearing part.

4. The dispensing assembly according to claim 1, wherein a removable protective cap is mounted on said body.

5. The dispensing assembly according to claim 4, wherein said protective cap comprises an axial extension cooperating with said actuation element to prevent its pivoting.

6. The dispensing assembly according to claim 1, wherein said pivot axis extends radially outside said reservoir.

7. The dispensing assembly according to claim 1, wherein said pivot axis is arranged substantially secant to the longitudinal central axis of said reservoir.

8. The dispensing assembly according to claim 1, wherein the fluid product dispenser is as a nasal dispensing device.

* * * * *